United States Patent [19]
Wunderlich et al.

[11] Patent Number: 5,116,974
[45] Date of Patent: May 26, 1992

[54] 3-CARBALKOXYAMINO-5-AMINOACYL-5H-DIBENZ[B,F]AZEPINES, AND METHODS FOR MAKING

[75] Inventors: Helmut Wunderlich, Dresden; Andreas Stark, Radebeul; Lothar Zenker, Radebeul; Dieter Lohmann, Radebeul; Hildegard Poppe; Reni Bartsch, both of Dresden, all of German Democratic Rep.; Aleksandr P. Skoldinov, Moskau, U.S.S.R.; Natalja V. Kaverina, Moskau, U.S.S.R.; Anna N. Grizenko, Moskau, U.S.S.R.; Valentin V. Lyskovzev, Moskau, U.S.S.R.

[73] Assignee: Arzneimittelwerk Dresden GmbH, Radebeul, Fed. Rep. of Germany

[21] Appl. No.: 546,590

[22] Filed: Jun. 29, 1990

[30] Foreign Application Priority Data

Jun. 30, 1989 [DD] German Democratic Rep. ... 330174

[51] Int. Cl.$^5$ .......................................... C07D 223/22
[52] U.S. Cl. .................................... 540/591; 540/589
[58] Field of Search ................. 540/589, 591; 514/217

[56] References Cited

PUBLICATIONS

Wunderlich et al, Pharmazie 40(12), 827–30, 1985.
Kaverina et al, Pharmazie 40(12), 830–32, 1988.

*Primary Examiner*—John M. Ford
*Assistant Examiner*—Y. Gupta
*Attorney, Agent, or Firm*—Schweitzer Cornman & Gross

[57] ABSTRACT

New 3-carbalkoxyamino-5-aminoacyl-5H-dibenz[b,-f]azepines and their pharmaceutically acceptable acid addition salts, and methods for their synthesis are described. These compounds are useful as antiarrhythmic agents in the treatment of heart disorders. The new compounds are made by reacting a 3-carbalkoxyamino-5-halogenacyl-5H-dibenz[b,f]azepines with an amine to form the desired target product, which can be optionally converted into its pharmaceutically acceptable acid addition salt.

4 Claims, No Drawings

3-CARBALKOXYAMINO-5-AMINOACYL-5H-DIBENZ[B,F]AZEPINES, AND METHODS FOR MAKING

FIELD OF THE INVENTION

The present invention relates to new 3-carbalkoxyamino-5-aminoacyl derivatives of the 5H-dibenz[b,f,]azepine, to their pharmaceutically acceptable acid addition salts, and to methods for their preparation. The compounds have valuable antiarrhythmic effects and can be used for the therapy of heart disorders (arrhythmia).

BACKGROUND OF THE INVENTION

The new compounds of the present invention have not been described previously. The synthesis only of 3-carbethoxyamino-5-methylamino-acetyl-10,11-dihydro-5H-dibenz[b,f]azepine has been described (Die Pharmazie 40/1985, 825–835), but not with reference to its pharmacological action.

Of the structurally related 3-carbalkoxyamino-5-dialkylaminoacyl-10,11-dihydro-5H-dibenz[b,f]azepines, 3-carbethoxyamino-5-dimethylaminoacetyl-10,11-dihydro-5H-dibenz[b,f]azepine described in (German Democratic Republic patent No. 152,782; Soviet Patent No. 1,089,089), is undergoing clinical trials at the present time. The new compounds of the present invention differ from these known ones basically due to the amine group, which is a tertiary amino group in the compounds of the aforementioned literature, but is a primary or secondary amino group in the compounds of the present invention.

It is well known that this decisive structural difference not only requires different chemical processes for the synthesis but also is associated with new factors with respect to the pharmacological effects of the compounds of the present invention. This is true particularly for the behavior of such compounds in the course of the biological degradation and metabolism in the organism, as evidenced by the remarkable effect on absorption, distribution, biotransformation and elimination and, with that, on the character and duration of the resulting effect.

Numerous other antiarrhythmic drugs are known, which are used on a more or less broad scale in the therapy of heart disorders. These include, quinidine, lidocaine, mexiletin, verapamil, propafenone, disopyramide, morazicine and etazicine. In some cases greater differences in the chemical structures of these materials do not reveal any generally valid rules for describing structure-effect relationships. The generally known therapeutic drugs are not structurally related to the compounds of the present invention.

DESCRIPTION OF THE INVENTION

The present invention enables the synthesis of new, highly effective cardiovascular pharmaceuticals, which, because of their pronounced antiarrhythmic effect, can be used in the therapy of heart disorders. Not only is a high effectiveness and specificity of action achieved with the compounds of the present invention, but disadvantages in the biotransformation of existing compounds are avoided. This has an advantageous effect on the duration of action.

Aside from the high effectiveness, the good tolerance of the compounds of the invention, particularly, the absence of unfavorable phychotropic effects, such as sedation and central excitation, contribute to the improvement in the safety of the therapy in the treatment of arrhythmic heart disorders.

The present invention relates to new 3-carbalkoxyamino-5-aminoacyl derivatives of the 5H-dibenz[b,f]azepine of formula I,

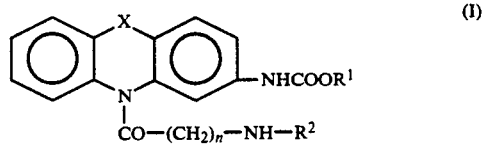

wherein
$R^1$ is a straight chain, or branched $C_{1-3}$ alkyl residue,
$R^2$, aralkyl, or a $C_2$ alkoxy residue, residue, or an aralkyl group, such as benzyl or phenylethyl, or a β-oxyethyl group.
n is a cardinal number from 1 to 5, and
X is a $-CH_2-CH_2-$, or $-CH=CH-$ residue,
and to their pharmaceutically acceptable acid addition salts, provided that when $R^2$ is methyl, then $R^1$ is methyl or isopropyl, or is a cardinal number from 2 to 5.

Pursuant to the invention, the new compounds of the invention are prepared by reacting a 5-halogenacyl-3-carbalkoxyamino-5H-dibenz[d,f]-azepine of formula II,

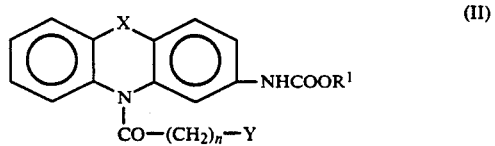

wherein $R^1$, $R^2$, n and X have the meaning given above, and Y is Cl or Br with an amine of formula III,

wherein $R^2$ has the meaning previously given.

The starting materials of formula II are known. For example, according to the aforementioned German Democratic Republic and Soviet patents cited, they can be obtained from 3-carbalkoxyamino-5H-dibenz[b,f]azepines by reaction with a halogenacyl halide.

The amines of formula III are easily obtainable industrially, such as ammonia, methylamine, ethylamine, n-propylamine, beta-oxyethylamine, n-hexylamine, as well as isopropylamine, t-butylamine, cyclohexylamine, benzylamine and phenylethylamine. The amines can be used in pure form as well as in the form of their solutions in organic solvents or also in aqueous solution.

The reaction of the reactants to form the new compounds of formula I is suitably carried out in the presence of solvents. Suitably low molecular weight alcohols, such as methanol, ethanol, n-propanol or neutral aliphatic or aromatic hydrocarbons, such as cyclohexane, benzene, toluene or also halogenated hydrocarbons, such as chloroform, carbon tetrachloride or chlorobenzene are employed as solvents for that purpose.

The amines of formula III can be used in pure form, such as gaseous ammonia, or also as their solutions in the aformentioned solvents. It is also possible, and may sometimes be of advantage to use these amines as aqueous solutions. This is especially so for ammonia, methylamine and ethylamine.

The reactions for preparing compounds of the invention can be carried out at room temperature, or at elevated temperatures up to the boiling point of the solvent or solvent mixture.

Since hydrohalide of compounds of formula II is formed during the reaction of the present invention with amines of formula III, suitably hydrohalide acceptors are also employed. Conventional inorganic compounds, such as soda or potash, or also tertiary amines, such as triethylamine or pyridine, are suitable for this purpose. It is particularly advantageous to use the amine of formula III in an appropriate excess to bind the hydrohalide. During the reaction of the halogenacyl derivatives of formula II with an amine of formula III, in a side reaction a compound of formula IV is formed, It is obvious to those skilled in the art that the base compounds of formula I can be released from their acid addition salts by the action of basically reacting materials, such as alkali carbonates, alkali hydroxides, amines or ammonia in a known manner, this process being used preferably in the course of purifying operations.

The new 5H-dibenz[b,f]azepines of formula I are distinguished in animal experiments by a pronounced antiarrhythmic effect. In various pharmacological models for testing the antiarrhythmic effectiveness, the new compounds of the present invention proved to have a significantly stronger action than other therapeutic agents, such as lidocaine, mexiletin and morazicine, which have been used in the treatment of heart disorders. In particular, the inventive compounds show advantageous effects even in comparison to the structurally related 10,11-dihydro-5H-dibenz[b,f]azepines, which are described in German Democratic Republic patent No. 152,782 and in Soviet Patent No. 1,089,089

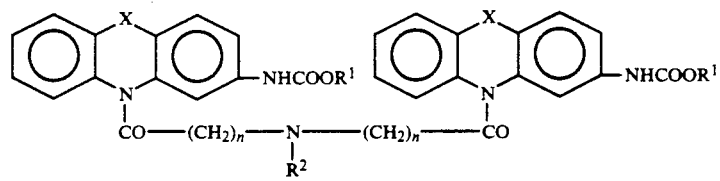

(IV)

wherein X, n, $R^1$ and $R^2$ have the same meaning as above. To suppress that side reaction it is advisable to use a stiochiometric excess of the amine of formula III for binding the halogen halide. Generally, a favorable course of the reaction is achieved, if an excess of the amine of formula III of up to 800% is chosen, a higher excess to be used particularly if the reactants are rather volatile amines such as ammonia or methylamine. It is also possible to carry out the reaction without the use of any hydrohalide acceptors. In such case the compound of formula I, which is formed, can itself function as a hydrohalide acceptor, so that the compounds of formula I will be obtained directly in the form of their hydrohalide salts.

The reaction products of formula I are oily or crystalline materials, which can exist as hydrates in the presence of water or humidity. The compounds are soluble in the common organic solvents and only slightly soluble in water.

For medical applications, the compounds of the present invention are suitably employed in the form of their water soluble, pharmaceutically acceptable acid addition salts, such as obtained with hydrochloric acid, sulfuric acid, tartaric acid, citric acid, etc. These salts can be synthesized in a known manner and can be optionally also hydrated.

and of which the 3-carbethoxyamino-5-dimethylaminoacetyl-10,11-dihydro-5-H-dibenz[b,f]-azepine is currently undergoing clinical trials.

Since there is even a significant improvement in the therapeutic breadth, as demonstrated by the aconitine model involving the rat (see the Table I, $Q = LD_{50\ i.v.}/ED_{73\ i.v.}$), while the tolerance is about the same and the effectiveness is increased, the new compounds of the invention are available to advantage for the treatment of heart disorders.

Despite a tricyclic structure related to psychopharmaceutical drugs, the present compounds are well tolerated, neither sedating nor centrally exciting or other emotionally unfavorable effects can be detected in the case of the new compounds of the present invention.

It is also emphasized that, in comparative investigations of the 2-step coronary ligature in dogs (Harris model), the new compounds of formula I have an advantageously sustained duration of action (see Table 1).

Various pharmaceutical dosage forms, such as uncoated or coated tablets, drip solutions or injections and other forms are suitable in the therapy of heart disorders. Depending on the degree of severity of the disorder, the dose, which can be administered orally once or several times daily, can vary on the average from about 5 to about 100 mg.

TABLE 1

| No. | n | x | $R^1$ | $R^2$ | aconitine rat $ED_{73}$ i.v. mg/kg | acute tox. rat $LD_{50}$ i.v. mg/kg | Q | Harris eff. dose mg/kg i.v. | dog duration of action min |
|---|---|---|---|---|---|---|---|---|---|
| 1 | 1 | $-CH_2-CH_2-$ | $-C_2H_5$ | $-CH_2-C_6H_5$ | 0.79 (0.53–1.2) | 13 (12–13) | 16 | — | — |
| 2 | 1 | $-CH_2-CH_2-$ | $-C_2H_5$ | $-CH_2-CH_2-OH$ | 0.19 (0.12–0.29) | 12 (11–13) | 63 | 2.0 | 60 |
| 3 | 1 | $-CH_2-CH_2-$ | $-C_2H_5$ | $-C_2H_5$ | 0.09 (0.048–0.17) | 9.6 (8.6–11) | 107 | 1.0 2.0 | 60 180 |

TABLE 1-continued

| No. | n | x | $R^1$ | $R^2$ | aconitine rat $ED_{73}$ i.v. mg/kg | acute tox. rat $LD_{50}$ i.v. mg/kg | Q | Harris eff. dose mg/kg i.v. | dog duration of action min |
|---|---|---|---|---|---|---|---|---|---|
| 4 | 1 | $-CH_2-CH_2-$ | $-C_2H_5$ | $-C_3H_7$(iso) | 0.71 (0.40–1.3) | 8.2 (7.8–8.7) | 12 | — | — |
| 5 | 1 | $-CH_2-CH_2-$ | $-C_2H_5$ | $-C_3H_7$(normal) | 0.18 (0.12–0.28) | 6.1 (5.6–6.8) | 34 | — | — |
| 6 | 1 | $-CH_2-CH_2-$ | $-C_2H_5$ | $-C_4H_9$(tert.) | 0.35 (0.23–0.54) | 5.6 (5.2–6.0) | 16 | — | — |
| 7 | 1 | $-CH_2-CH_2-$ | $-C_2H_5$ | $-C_4H_9$(normal) | 0.29 (0.19–0.45) | 5.0 (4.0–6.3) | 17 | — | — |
| 8 | 1 | $-CH_2-CH_2-$ | $-C_2H_5$ | -Cyclohexyl | 0.25 (0.18–0.33) | 3.7 (3.2–4.4) | 15 | — | — |
| 9 | 1 | $-CH_2-CH_2-$ | $-C_2H_5$ | $-C_6H_{13}$(normal) | 0.90 (0.48–1.7) | 14 (13–16) | 16 | — | — |
| 10 | 1 | $-CH_2-CH_2-$ | $-C_2H_5$ | $-H$ | 0.20 (0.13–0.32) | 14 (13–15) | 70 | — | — |
| 11 | 1 | $-CH_2-CH_2-$ | $-C_3H_7$(iso) | $-CH_3$ | 0.61 (0.40–0.93) | 15 (15–16) | 25 | — | — |
| 12 | 1 | $-CH_2-CH_2-$ | $-C_3H_7$(iso) | $-CH_2-CH_2-OH$ | 0.51 (0.33–0.80) | 20 (19–22) | 39 | — | — |
| 13 | 1 | $-CH_2-CH_2-$ | $-C_3H_7$(iso) | $-C_2H_5$ | 0.47 (0.24–0.9) | 16 (14–17) | 34 | — | — |
| 14 | 1 | $-CH_2-CH_2-$ | $-C_3H_7$(iso) | $-C_4H_9$(tert.) | 0.18 (0.14–0.23) | — | — | — | — |
| 15 | 1 | $-CH_2-CH_2-$ | $-CH_3$ | $-CH_3$ | 0.30 (0.075–1.2) | 20 (19–22) | 67 | 2.0 | 15 |
| 16 | 1 | $-CH_2-CH_2-$ | $-CH_3$ | $-CH_2-CH_2-OH$ | 0.40 (0.29–0.55) | 36 (28–45) | 90 | — | — |
| 17 | 1 | $-CH_2-CH_2-$ | $-CH_3$ | $-C_2H_5$ | 0.95 (0.35–2.6) | 19 (16–21) | 20 | 2.0 | 15 |
| 18 | 2 | $-CH_2-CH_2-$ | $-C_2H_5$ | $-CH_2-CH_2-OH$ | 0.85 (0.50–1.5) | 20 (17–20) | 24 | 2.0 | 60 |
| 19 | 1 | $-CH=CH-$ | $-C_2-H_5$ | $-CH_3$ | 0.32 (0.20–0.49) | 11 (9.6–12) | 34 | — | — |
| 20 | 1 | $-CH=CH-$ | $-C_2H_5$ | $-C_2H_5$ | 0.40 (0.25–0.64) | 6.2 (5.8–6.5) | 15 | — | — |
| 21 | 2 | $-CH_2-CH_2-$ | $-C_2H_5$ | $-C_2H_5$ | 0.42 (0.24–0.75) | 12 (11–13) | 29 | — | — |
| 22 | 1 | $-CH_2-CH_2-$ | $-C_2H_5$ | $-CH-$<br>$CH_3$ | 3.5 (2.1–5.8) | 31 (29–34) | 9 | — | — |
| | | | | Lidocaine | 9.2 (5.9–15) | 18 (17–21) | 2.0 | 6.0 | 10 |
| | | | | Morazicine | 1.1 (0.41–3.1) | 11 (9.6–12) | 10 | 2.0 | 15 |
| | | | | Bonnecor ® | 0.28 (0.13–0.62) | 11 (10–12 | 39 | 2.0 | 15 |
| | | | | Mexiletin | 15 (8.8–25) | 41 (34–50) | 2.7 | — | 11 |

In Table 1:

$ED_{73\ i.v.}$ = the dose in mg/kg, which inhibits aconitine arrhythmia in female Wistar rats after i.v. administration of the test substance up to the occurrence of isolated ventricular extrasystolea (K. Femmer et al., Pharmazie 31, page 36 (1976). The data is analyzed by the Probit regression analysis with a confidence interval of p=0.05 (values given in parentheses).

$LD_{50\ i.v.}$ = lethal dose in mg/kg for 50% of the experimental animals of an orientating acute toxicity test on male or female Wistar rats of our own breed, i.v. administration in the tail vein, 3–4 dosages, 10 animals per group. Data analyzed by the Probit regression analysis with a confidence interval of p=0.05 (values given in parentheses).

eff. dose = effective dose in mg/kg, as well as duration of action in minutes on dogs, 24 hours after a 2-step coronary ligature (Kaverina et al., Pharmazie 12, page 845, 1985) = ratio of $LD_{50\ i.v.}/ED_{73\ i.v.}$ for determining the width of therapeutic effect.

EXAMPLE 1

Preparation of 3-carbethoxyamino-b 5-benzylaminoacetyl-10,11-dihydro-5H-dibenz[b,f]azepine 18 g, 0.05 moles of 3-carbethoxyamino-5-chloroacetyl-10,11-dihydro-5H-dibenz[b,f]azepine (hereafter referred to as "Startazepine 1" is suspended in 120 ml ethanol in a 500 ml 3-neck flask with stirring and, after addition of 20 g of benzylamine (approximately 0.2 moles) heated to boiling for 4–5 hours on a water bath. After about 1 hour, the solution becomes almost clear. Benzylamine hydrochloride does not precipitate during the reaction. The reaction mixture is allowed to stand overnight with cooling. During this time, there is good crystallization. After filtering with suction, the filter-cake is washed with ethanol and water to remove the benzylamine hydrochloride.

Melting Point: 155° C.–157° C. The base is not very soluble in dilute acids.

Molecular weight is 429.52

| Elementary analysis: | | | |
|---|---|---|---|
| calculated: % | C = 72.70 | H = 6.34 | N = 9.78 |
| found: % | 72.63 | 6.53 | 9.75 |
| | 72.63 | 6.54 | 9.79 |

EXAMPLE 2

Preparation of
3-carbethoxyamino-5-(beta-oxyethylamino)acetyl-10,11-dihydro-5H-dibenz[b,f]azepine 36 g, 0.1 moles of Startazepine 1 is suspended in 200 ml of ethanol, mixed with 19 g (0.32 moles) of ethanolamine and refluxed for 4 hours. After hot filtration, the filtrate is evaporated to dryness and the remaining viscous residue is taken up in 100 ml of acetone. The clear, colorless acetone solution is treated with isopropanolic hydrochloric acid until pH 2 to 3, and is then crystallized in a refrigerator. The crystals are filtered off, with suction, washed with a little acetone and dried. Yield 25 g = 59.5% of the theoretical yield. Melting point of the crude material: 204° C. to 208° C. Recrystallization from an isopropanol/ethanol mixture with addition of activated charcoal. Yield of recrystallized material: 15 g
Melting point: 219° C. to 224° C.

| Elementary analysis: | | | | |
|---|---|---|---|---|
| calculated: % | C = 60.06 | H = 6.24 | N = 10.01 | Cl = 8.44 |
| found: % | 59.79 | 6.33 | 9.80 | 8.41 |
| | 59.84 | 6.27 | 9.82 | 8.55 |

EXAMPLE 3

Preparation of
3-carbethoxy-5-monoethylamino-acetyl-10,11-dihydro-5H-dibenz[b,f]azepine A suspension of 72 g (0.2 moles) of Startazepine 1 in 1,000 ml of ethanol (96%) is stirred and mixed with 150 g of 30% aqueous monoethylamine solution (1 mole). Stirring is then continued, at first for 1 hour at 60° C. and then for 4 hours at 70° C. to 75° C. The mixture is slightly cooled and poured into 2,500 ml of an ice/water mixture and crystallization is induced after prolonged standing. The crystals are filtered with suction and washed with water until free of amine.
Yield is 7 g = 96.6% of the theoretical yield. Melting point of the crude material: 152° C. to 159° C.
After recrystallization from acetone (1 g from 10 ml), the melting point of the resulting crystals is 157° C. to 160° C. Empirical formula is $C_{21}H_{25}N_3O_3$, and the molecular weight is 367.45.

| Elementary analysis: | | | |
|---|---|---|---|
| calculated: % | C = 68.64 | H = 6.86 | N = 11.44 |
| found: % | 68.63 | 6.93 | 11.22 |
| | 68.67 | 7.01 | 11.26 |

EXAMPLE 4

Preparation of
3-carbethoxyamino-5-isopropylamino-acetyl-10,11-dihydro-5H-dibenz[b,f]azepine A suspension of 36 g (0.1 moles) of Startazepine 1 in 250 ml of ethanol (96%) is mixed with 18 g (0.3 moles) of isopropylamine and the mixture is refluxed for 5 hours. After hot filtration, the filtrate is evaporated to dryness and the viscous residue is taken up in 250 ml of chloroform and shaken twice with 100 ml of water. The chloroform phase is once more evaporated to dryness and the spongy residue is dissolved in 400 ml of cold acetone. On prolonged standing, 10.5 g (=25% of the theoretical yield) of a slightly yellow substance crystallize out. Melting point is 224° C. to 228° C. (after recrystallization from ethanol).

| Elementary analysis of the hydrochloride | | | | |
|---|---|---|---|---|
| calculated: % | C = 63.22 | H = 6.75 | N = 10.05 | Cl = 8.48 |
| found: % | 63.18 | 6.86 | 9.99 | 8.28 |
| | 63.24 | 6.96 | 10.20 | 8.38 |

EXAMPLE 5

Preparation of
3-carbethoxyamino-5-n-propylamino-acetyl-10,11-dihydro-5H-dibenz[b,f]azepine A suspension of 36 g (.1 moles) of Startazepine 1 in 250 ml of ethanol (96%) is mixed with 20 g (approximately 0.33 moles) of n-propylamine and refluxed for 4 to 5 hours. Subsequently 80 to 100 ml of ethanol are distilled off from the reaction mixture and the remaining solution, which is filtered hot, is induced to crystallize after prolonged standing. The crystals are filtered off with suction and washed with a little alcohol. The yield is 25 g, i.e. 65.5% of the theoretical yield. The melting point is 156° C. to 160° C. Empirical formula is $C_{22}H_{27}N_3O_3$, and the molecular weight is 381.48

| Elementary analysis of the base compound | | | |
|---|---|---|---|
| calculated: % | C = 69.27 | H = 7.13 | N = 11.01 |
| found: % | 69.18 | 7.15 | 10.81 |
| | 69.04 | 7.15 | 10.78 |

EXAMPLE 6

Preparation of
3-carbethoxyamino-5-tertiary-butylamino-acetyl-10,11-dihydro-5H-dibenz[b,f]azepine A suspension of 36 g (0.1 moles) of Startazepine 1 in 250 ml of ethanol is mixed with 22 g (0.3 moles) of tertiary butylamine. The mixture is refluxed for 5 hours. After cooling, approximately 8 g of unreacted startazepine 1 are filtered off with suction. The clear filtrate is mixed with twice the amount of water and the precipitated product is filtered off with suction (29 g). After purification by reprecipitation (from 250 ml of 1N HCl and 250 ml of ethanol, the base is precipitated, after filtration, with NH₃), 27 g of crude product are obtained. This is dissolved in 150 ml of ethanol and 70 ml of 1N HCl and, after filtration, evaporated under vacuum to dryness. The entire of the residue is refluxed for 30 minutes with 200 ml of acetone. The undissolved material is filtered off with suction and the filtrate is allowed to stand until crystallization takes place. Upon prolonged standing, 13 g (28.9% of the theoretical) are obtained as colorless crystals.
Melting point is 182° C. to 196° C.

| Elementary analysis of the hydrochloride hydrate | | | | |
|---|---|---|---|---|
| calculated: % | C = 61.39 | H = 7.16 | N = 9.34 | Cl = 7.88 |

-continued

| Elementary analysis of the hydrochloride hydrate | | | |
|---|---|---|---|
| found: % | 61.46 | 7.20 | 9.61 | 7.82 |
| | 61.53 | 7.17 | | 8.01 |

EXAMPLE 7

Preparation of
3-carbethoxyamino-5-n-butylamino-acetyl-10,11-dihydro-5H-dibenz[b,f]azepine A suspension of 36 g (0.1 moles) of Startazepine 1 in 250 ml of ethanol is mixed with 30 g (0.4 moles) of n-butylamine and refluxed for 4 hours. Subsequently, about 50 ml of ethanol are distilled off and, after filtering hot, the whole of the solution is placed in a refrigerator. The crystals formed are filtered off with suction, washed with a little alcohol and dried. The yield is 33 g, i.e. 83.4% of the theoretical yield. The melting point is 184° C. to 188° C.

| Elementary analysis of the base compound: | | | |
|---|---|---|---|
| calculated: % | C = 69.95 | H = 7.39 | N = 10.62 |
| found: % | 61.78 | 7.50 | 10.40 |
| | 69.75 | 7.55 | 10.70 |

EXAMPLE 8

Preparation of
3-carbethoxyamino-5-cyclohexylamino-acetyl-10,11-dihydro-5H-dibenz[b,f]azepine A suspension of 36 g (0.1 moles) of Startazepine 1 in 250 ml of toluene is mixed with 30 g (0.3 moles) of cyclohexylamine and refluxed for 4 hours. The precipitated cyclohexylamine hydrochloride is filtered with suction from the still hot solution. The filtrate is washed with water until free of amine and, after being dried over sodium sulfate, evaporated to dryness. The residue is dissolved in a mixture of 100 ml of 2N HCl and 50 ml of ethanol and induced to crystallize the crystalline material is filtered off with suction, washed with the same HCl/ethanol mixture and dried. The yield is 38.5 g. The melting point of the crude material is 167° C. to 175° C.

The entirety of the product is next boiled out with 400 ml of acetone. The yield is 27 g, or 56.7% of the theoretical yield. The melting point is 182° C. to 188° C.

| Elementary analysis of the hydrochloride hydrate | | | | |
|---|---|---|---|---|
| calculated: % | C = 63.08 | H = 7.20 | N = 8.83 | Cl = 7.45 |
| found: % | 61.78 | 7.23 | 8.75 | 7.57 |
| | | | 8.83 | 7.45 |

EXAMPLE 9

Preparation of
3-carbethoxyamino-5-cyclohexylamino-acetyl-10,11-dihydro-5H-dibenz[b,f]azepine A suspension of 36 g (0.1 moles) of Startazepine 1 in 250 ml of ethanol is mixed with 35 g (0.35 moles) of n-hexylamine and refluxed for 4 hours. Subsequently it is evaporated to dryness. The residue is shaken with 200 ml of CHCl₃ and 400 ml of warm water, the chloroform phase is separated, extracted once more with water and, after being dried over sodium sulfate, distilled to dryness once again. The residue is boiled in 250 ml of isopropanol containing 2 g of activated charcoal, filtered hot with suction and allowed to stand to crystallize. The yield is 18.5 g, or 43.7% of the theoretical yield. The melting point is 121° C.–123° C. of the base compound.

| Elementary analysis of the base compound | | | |
|---|---|---|---|
| calculated: % | C = 70.89 | H = 7.85 | N = 9.92 |
| found: % | 70.71 | 7.80 | 9.98 |
| | 70.91 | 7.90 | 9.91 |

EXAMPLE 10

Preparation of
3-carbethoxyamino-5-amino-acetyl-10,11-dihydro-5H-dibenz[b,f]azepine A suspension of 1.75 g (0.005 moles) of Startazepine 1 in 50 ml of ethanol and 1.7 g (0.1 ) of ammonia is shaken in an autoclave for 3 hours at 56° C. to 58° C. and then heated for a further 4 hours at 140° C. to 150° C. After cooling, the reaction mixture is concentrated under vacuum and the residue obtained is dissolved in about 120 ml of 5% HCl. The acidic solution is cleaned up by the addition of a little activated charcoal, made alkaline with dilute sodium hydroxide solution and the base obtained is recrystallized from toluene. The yield is 1.12 g, or 68% of the theoretical yield. The melting point is 158° C. to 159° C.

| Elementary analysis of the base compound | | | |
|---|---|---|---|
| calculated: % | C = 67.24 | H = 6.24 | N = 12.38 |
| found: % | 67.62 | 6.38 | 12.51 |

EXAMPLE 11

Preparation of
3-carbethoxyamino-5-cyclohexylamino-acetyl-10,11-dihydro-5H-dibenz[b,f]azepine 18 g, approximately 0.05 moles of 3-carbisopropoxyamino-5-chloroacetyl-10,11-dihydro-5H-dibenz[b,f]azepine (hereafter referred to as Startazeine 2) and 300 ml of 96% ethanol are added to a 2liter 3-neck flask. At room temperature, 100 ml of aqueous monomethylamine solution (38%=1.2 moles) are added with stirring. The reaction mixture is heated slowly by means of a water bath to 50° C., stirred for 3 hours at this temperature and then for another hour at 60° C. After cooling to 25° C.–30° C., 750 ml of cold water are added. After standing overnight, an additional 400 ml of water are added with stirring. The water-amine-alcohol mixture is decanted from the oily deposit formed and same amount of fresh water is added. After decanting the supernatant once more, the oily residue is dissolved in 80 ml of warm acetone, cleaned through a filter and induced to crystallize in the refrigerator. The yield is 11 g, or 60% of the theoretical yield. The melting point is 150° C.–152° C. The empirical formula is $C_{21}H_{25}N_3O_3$, and the molecular weight is 367.46.

| Elementary analysis: | | | |
|---|---|---|---|
| calculated: % | C = 68.62 | H = 6.86 | N = 11.38 |
| found: % | 68.66 | 6.91 | 11.25 |

-continued

Elementary analysis:

| | | |
|---|---|---|
| 68.74 | 6.98 | 11.39 |

EXAMPLE 12

Preparation of
3-carbethoxyamino-5-($\beta$-oxyethyamino)-acetyl-10,11-dihydro-5H-dibenz[b,f]azepine A suspension of 3.7 g (0.01 moles) of Startazepine 2 in 60 ml of toluene is refluxed for 4 hours with 3 g (0.05 moles) of ethanolamine. After cooling and extracting with water, the precipitated oil is separated and recrystallized from ethyl aceate, 2.5 g, or 57% of the theoretical yield of base are obtained, with a melting point of 138° C.–149° C.

Elementary analysis:

| calculated % | found % |
|---|---|
| N = 10.57 | 10.81 |

The hydrochloride salt formed from toluene and ethereal HCl, has a melting point of 160° C. (decomposition)

Elementary analysis:

| calculated % | found % |
|---|---|
| N = 9.68 | 9.30/9.34 |
| Cl = 8.16 | 7.80/7.90 |

EXAMPLE 13

Preparation of
3-carbisopropoxyamino-5-ethylamino-acetyl-10,11-dihydro-5H-dibenz[b,f]azepine A suspension of 3.7 g (0.01 moles) of Startazepine 2 in 35 ml of toluene is stirred for 5 to 7 hours at 50° C. with 10 g (0.04 moles) of a 33% aqueous ethylamine solution. After cooling and washing with water, the toluene phase is evaporated and the remaining residue is recrystallized from 20 ml of isopropanol. The obtained yield is 2.35 g, or 61% of the theoretical. The melting point is 152° C. to 153° C.

Elementary analysis:

| calculated % | found % |
|---|---|
| C = 69.26 | 69.22/69.37 |
| H = 7.13 | 7.17/7.23 |

The hydrochloride salt is obtained from toluene and ethereal HCl. The melting point is 180° C. to 185° C. when recrystallized from isopropanol.

EXAMPLE 14

Preparation of
3-carbethoxyamino-5-tert.-butylamino-acetyl-10,11-dihydro-5H-dibenz[b,f]azepine A suspension of 3.7 g (0.01 moles) of Startazepine 2 in 30 ml of ethanol is refluxed for 4 hours with 3.6 g (0.05 moles) of tertiary butylamine. After working it up, 3 g of the base compound, corresponding to 75% of the theoretical yield, are obtained. The melting point is 154° C. to 156° C. when recrystallized from toluene.

Elementary analysis:

| | | | |
|---|---|---|---|
| calculated: % | C = 67.35 | H = 7.77 | N = 9.83 |
| found: % | 67.61 | 7.53 | 9.84 |

The hydrochloride salt is formed from isopropanol and ethereal HCl. Its melting point is 185° C. to 187° C.

Elementary analysis:

| | | | |
|---|---|---|---|
| calculated: % | C = 62.12 | H = 7.16 | Cl = 7.64 |
| found: % | 62.42 | 7.22 | 7.21 |

EXAMPLE 15

Preparation of
3-carbethoxyamino-5-methylamino-acetyl-10,11-dihydro-5H-dibenz[b,f]azepine 2.4 g, 0.006 moles of 3-carbmethoxyamino-5-chloroacetyl-10,11-dihydro-5H-dibenz[b,f]azepine (hereafter referred to as "Startazepine 3") is shaken with 1.2 g (0.04 moles) of methylamine in 30 ml of toluene for 3 hours in an autoclave at 40° C. to 50° C. and is subsequently heated for 4 hours at 150° C. to 155° C. After working it up, and precipitation of a hydrochloride in toluene with ethereal HCl, 1,2 g, corresponding to 46% of the theoretical yield, are obtained, having a melting point of 254° C. to 256° C.

Elementary analysis:

| | | | |
|---|---|---|---|
| calculated: % | C = 60.72 | H = 5.89 | N = 11.18 |
| found: % | 61.15 | 5.98 | 11.38 |

EXAMPLE 16

Preparation of
3-carbethoxyamino-5-$\beta$-oxyethylamino-acetyl-10,11-dihydro-5H-dibenz[b,f]azepine 2.4 g, 0.006 moles of Startazepine 3 is refluxed for 4 hours with 1.8 g (0.03 moles) of ethanolamine in 70 ml toluene. After working it up, an oily base is obtained, which is precipitated as hydrochloride in toluene with ethereal HCl. Its melting point is 220° C. after recrystallization from ethanol.

Elementary analysis:

| | | | |
|---|---|---|---|
| calculated: % | C = 57.93 | H = 6.14 | Cl = 9.00 |
| found: % | 57.57 | 6.04 | 9.16/9.26 |

EXAMPLE 17

Preparation of
3-carbethoxyamino-5-ethylamino-acetyl-10,11-dihydro-5H-dibenz[b,f]azepine 7 g, 0.02 moles of Startazepine 3 is suspended in 120 ml of toluene and mixed with 25 g (0.18 moles) of a 33% aqueous ethylamine solution. The temperature is raised within an hour to 50° C. and, after addition of 30 ml of ethanol for solubility improvement, it is refluxed for 4 hours. After working it up, the oily residue is dissolved in isopropanol and the hydrochloride is precipitated with isopropanolic HCl. The yield is 5 g, corresponding to 63% of the theoretical yield. The melting point is 241° C. to 243° C.

| Elementary analysis: | | | |
|---|---|---|---|
| calculated: % | C = 61.61 | H = 6.20 | Cl = 9.09 |
| found: % | 61.30 | 6.38 | 9.09 |

EXAMPLE 18

Preparation of 3-carbethoxyamino-5-$\beta$-($\beta$-oxyethylamino-propionyl-10,11-dihydro-5H-dibenz[b,f]azepine 1.75 g, 0.01 moles of 3-carbethoxyamino-5-$\beta$-chloropropionyl-10,11-dihydro-5H-dibenz[b,f]azepine (hereafter referred to as "Startazepine 4", 3 g (0.05 moles of ethanolamine and 70 ml of ethanol are refluxed for 4 to 5 hours. After working it up, 3.4 g of the solid base are obtained. This base is dissolved in toluene and converted to the hydrochloride with ethereal HCl. The yield is 2.6 g, corresponding to 60% of the theoretical yield. The melting point is 186° C. to 187° C. (from isopropanol)

| Elementary analysis | |
|---|---|
| calculated % | found % |
| N = 9.68 | 9.90 |
| Cl = 8.17 | 7.98 |

EXAMPLE 19

Preparation of 3-carbethoxyamino-5-methylamino-acetyl-10,11-dihydro-5H-dibenz[b,f]azepine 12 g, 0.033 moles of 3-carbethoxyamino-5-chloroacetyl-5H-dibenz[b,f]azepine (hereafter referred to as "Startazepine 5") is suspended in 150 ml of ethanol. About 50 ml of an approximately 35% aqueous methylamine solution (about 0.5 moles of $CH_3NH_2$) are added and the mixture is stirred for 5 hours at 50° C. to 60° C., a clear, light yellow solution is formed. The reaction mixture is concentrated under vacuum to half the volume and then mixed with copious amounts of water. The oily precipitated base is extracted with chloroform (2×50 ml) and the organic phase is washed with water, dried over sodium sulfate and distilled to dryness under vacuum. A crystalline mass remains, which melts at 148° C. to 153° C., representing a yield of 7.2 g.

The base is dissolved in isopropanol and the hydrochloride is formed with isopropanolic HCl. The product is filtered off with suction, washed with a little acetone and dried. The yield is 6 g, corresponding to 46% of the theoretical yield, and the melting point is 243° C. to 270° C.

| Elementary analysis: | | | | |
|---|---|---|---|---|
| calculated: % | C = 61.22 | H = 5.78 | N = 10.71 | Cl = 9.04 |
| found: % | 61.03 | 6.16 | 10.90 | 9.02 |

EXAMPLE 20

Preparation of 3-carbethoxyamino-5-ethylamino-acetyl-acetyl-5H-dibenz[b,f]azepine To a suspension of 12 g of Startazepine 5 in 150 ml of ethanol, 70 ml of approximately 33% aqueous ethylamine solution are added and the mixture is stirred at 50° C. to 60° C. A clear, light yellow solution is formed. The reaction mixture is evaporated under vacuum to half its volume and mixed with copious amounts of water. The oily base produced is obtained by decanting the water phase. It is freed under vacuum from residual water. The residue of the base compound is dissolved in warm isopropanol. A small amount of cloudiness is filtered off from the solution, which is then acidified with isopropanolic HCl. After several days of standing in a refrigerator, the hydrochloride precipitates in crystalline form. It is filtered off with suction, washed with a little isopropanol and dried, yielding 11 g, corresponding to 83% of the theoretical yield.

Upon recrysallization from n-propanol (1:15) with addition of activated charcoal, a yield of 80%, colorless crystals is obtained, having a melting point of 234° C. to 240° C.

| Elementary analysis: | | | | |
|---|---|---|---|---|
| calculated: % | C = 62.76 | H = 6.02 | N = 10.46 | Cl = 8.82 |
| found: % | 62.52 | 6.36 | 10.42 | 8.57 |

EXAMPLE 21

Preparation of 3-carbethoxyamino-5-($\beta$-ethylaminopropionyl)-10,11-dihydro-5H-dibenz[b,f]azepine To a suspension of 37.3 g (0.1 moles) of Startazepine 4 in 250 ml of ethanol, 150 ml of an aqueous ethylamine solution are added. The mixture is stirred for 6 hours at 50° C. to 60° C. and then evaporated to dryness under reduced pressure. The residue is dissolved in 300 ml of 1N HCl. The solution obtained is treated at room temperature with activated charcoal and the base is precipitated by the addition of concentrated ammonia solution. The supernatant liquid is decanted off and the viscous product washed with water and taken up in ethyl ether. The pH is adjusted to 2 by the addition of isopropanolic HCl. Hydrochloride salt of the title compound crystallizes out with a yield of 36 g, having a melting point of approximately 150° C.

| Elementary analysis: | | | | |
|---|---|---|---|---|
| calculated: % | C = 60.61 | H = 9.94 | N = 9.6 | Cl = 8.13 |
| found: % | 60.69 | 9.94 | 9.73 | 8.00 |

EXAMPLE 22

Preparation of 3-carbethoxyamino-5-($\alpha$-phenylethylamino)-acetyl-10,11-dihydro-5H-dibenz[b,f]azepine 18 g, 0.05 moles of startazepine 1 in 150 ml of ethanol (96%) is mixed with 6 g (approx. 0.06 moles) triethylamine and 12 g of $\alpha$-phenylethylamine (approximately 0.1 moles) and refluxed for 6 to 8 hours. The clear yellow reaction solution is mixed with 700 to 800 ml of water and the oily deposit is isolated by decanting and taken up in 150 ml of acetone. The colorless acetone solution is made distinctly acidic with 10 ml of 2N HCl, cleaned up by being passed through a fluted filter paper and allowed to stand for crystallization. After filtration with suction, 22 g of hydrochloride, corresponding to 91.5% of the theoretical yield, are obtained, having a crude melting point of 144° C. to 152° C.

After recrystallization from ethanol and aqueous HCl 14 g, product melting at 155° C. to 161° C. are obtained, having the empirical formula of $C_{27}H_{32}N_3O_4Cl$.

| Elementary analysis of the hydrochloride hydrate salt, molecular weight 498 | | | | |
|---|---|---|---|---|
| calculated: % | C = 65.12 | H = 6.48 | N = 8.44 | Cl = 7.12 |
| found: % | 65.15 | 6.57 | 8.40 | 7.50 |
| | 65.12 | 6.58 | 8.52 | 7.60 |

We claim:

1. The compounds 3-Carbalkoxyamino-5-aminoacyl-5H-dibenz[b,f]azepines of formula I and their physiologically tolerated salts,

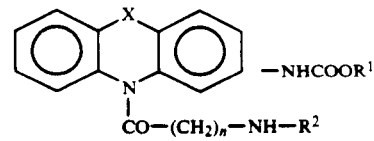

wherein
 $R^1$ is a straight chain, or branched $C_{1-3}$ alkyl residue,
 $R^2$ is hydrogen, or a straight chain, branched, or ring closed $C_{2-6}$ alkyl residue, or methyl residue, or an aralkyl group,
 n is a cardinal number from 1 to 5, and
 X is a —$CH_2$—$CH_2$—, or —CH=CH—residue,
and their pharmaceutically acceptable acid addition salts, provided that when $R^2$ is methyl, then $R^1$ is methyl or isopropyl or n is a cardinal number from 2 to 5.

2. A compound of claim 1, wherein the alkoxy group is methoxy, ethoxy, propoxy, or isopropoxy, said 5-amino group is a 5-benzylaminoacetyl, 5-(β-oxyethylamino0-acetyle, 5-isopropylaminnoacetyl,5-n-propylaminoacetyl, 5-tert.-butylaminoacetyl, 5-n-butylaminoacetyl, 5-cyclohexylaminoacetyl, 5-n-hexyaminoacetyl, 5-aminoacetyl, 5-methylaminoacetyl, 5-β-oxyethylaminoacetyl, 5-ethylaminoacetyl, 5-(β-ethylaminopropinyl)-acetyl, or 5-(α-phenylethylaminoacetyl group.

3. The compounds of claim 1, wherein said oralkyl group is a benzine, phenylethyl, or a β'-pxyethyl group.

4. A method for treating heart disorders, which comprises administering to a patient in need thereof a pharmaceutical containing as active ingredient a compound of claim 1.

* * * * *